United States Patent [19]

Sondahl et al.

[11] Patent Number: 4,810,649

[45] Date of Patent: * Mar. 7, 1989

[54] CONTROLLED REGENERATION OF ZEA DIPLOPERENNIS HYBRIDS AND BREEDING STRATEGIES THEREWITH

[75] Inventors: Maro R. Sondahl, Cherry Hill; David A. Evans, Palmyra; Laudenir Prioli, Delran, all of N.J.

[73] Assignee: DNA Plant Technology Corporation, Cinnaminson, N.J.

[*] Notice: The portion of the term of this patent subsequent to Apr. 21, 2004 has been disclaimed.

[21] Appl. No.: 13,403

[22] Filed: Feb. 11, 1987

Related U.S. Application Data

[63] Continuation-in-part of Ser. No. 597,472, Apr. 6, 1984, Pat. No. 4,659,668.

[51] Int. Cl.$^4$ ............................................. C12N 5/00
[52] U.S. Cl. ........................... 435/240.49; 435/240.5; 435/240.54
[58] Field of Search ........... 435/240.49, 240.5, 240.51, 435/240.54

[56] References Cited

U.S. PATENT DOCUMENTS 4,659,668 4/1987 Sondahl et al. .................. 435/240.5
4,677,246 6/1987 Armond et al. ........................ 800/1

OTHER PUBLICATIONS

"Maize and Cereal Protoplasts. Facts and Perspectives", Harms, C. T. In: Maize for Biological Research, pp. 373-384(1982).
"Plant Cell Culture and Somatic Cell Genetics of Cereals and Grasses", Vasil, I. K., Plant Improvement and Somatic Cell Genetics, pp. 179-203(1982).
"Chromosomal Variation and Frequency of Spontaneous Mutation Associated with In Vitro Culture and Plant Regeneration in Maize", Edallo, S., et al. Maydica 26:39-56(1981).
"Plant Regeneration from Tissue Cultures of Maize", Green, C. E. and R. L. Phillips, *Crop. Sci.*, 15:417-421(1975).
"Proliferation and Plant Regeneration from the Nodal Region of *Zea Mays L*. (Maize, Gramineae) Embryos", Vasil, V., et al., *Amer. J. Bot.* 70(6):951-954(1983).
"Tissue Culture of Maize. III Plantlet Regeneration from Scutellar Callus" Barthkowicak, E., *Genetica Polonica*, 23(3):93-101 (1981).
"Tissue Culture Regeneration of Plants in *Zea Dipoloperennis*, a Close Relative of Corn", Sondahl, M. R., et al., Bio/Technology, May:455-458(1984).

*Primary Examiner*—Charles F. Warren
*Assistant Examiner*—David T. Fox
*Attorney, Agent, or Firm*—Pennie & Edmonds

[57] ABSTRACT

This invention provides a method for high frequency plant regeneration from somatic stem donor tissue of field grown *Zea diploperennis*, a diploid, perennial corn ancestor with high tillering capacity. This species is used as a parent in a maize improvement strategy to transfer the unique traits of high tillering and plantlet regeneration capacity into cultivated corn. After 3-4 subcultures of cultured somatic tissues on a primary medium, small callus fragments are transferred to a secondary medium devoid of the auxin, 2,4-D. After a few days, numerous shoots regenerate and develop into normal plantlets which are then separated and transferred to a tertiary medium for root development. The selection of somaclonal variants form cultured somatic cells of interspecific hybrids between corn and teosinte are used for the synthesis of unique breeding lines suited for development of improved corn varieties. A protocol for gene transfer employing recombinant DNA techniques is also described.

16 Claims, 2 Drawing Sheets

CONTROLLED REGENERATION OF ZEA DIPLOPERENNIS HYBRIDS AND BREEDING STRATEGIES THEREWITH

CROSS-REFERENCE TO RELATED APPLICATIONS

This application is a continuation-in-part of U.S. application Ser. No. 597,472 filed Apr. 6, 1984 now U.S. Pat. No. 4,659,668.

FIELD OF THE INVENTION

This invention relates to the field of improvement of agricultural crop species. More specifically, the invention provides a method for the regeneration of an ancestral corn species and for the use of the regenerated plants in a commercial corn improvement program.

BACKGROUND OF THE INVENTION

The perfection of plant regeneration capabilities and the application of biotechnological techniques for genome modification provide a highly desirable system for the improvement of crop species.

Investigations concerning the morphogenesis of plant tissue in culture date back at least to the 1950's (Skoog, F. and Miller C. O., Symp Soc. Exp. Biol., 11:118 (1957)) and have continued apace to date. Several monographs provide extensive reviews of the field and contain compilations of numbers of species which will undergo plant regeneration in culture (See for example, Murashige T., In: "Propagation of Higher Plants through Tissue Culture," T. A. Thorpe, Ed., p. 15, Univ. Calgary Press, Calgary (1978); Vasil, I. K. et al. Adv. Gent. 20:127 (1979) and Evans, D. A., et al. In: "Plant Tissue Culture: Methods and Applications in Agriculture: T. A. Thorpe, Ed. pg. 45, Academic Press, N.Y. (1981)).

The impressive list of plants species cited in the above-referenced monographs, for which successful regeneration has been achieved, belies the difficulties in achieving those results. As will be noted later, successful regeneration of a particular species is often characterized by the addition of (or even omission of) catalytic amounts of auxins, cytokinins, or other growth regulators. Further, successful regeneration may also be a function of not only the mere presence of a certain compound but its ratio to other media components as well. Since each plant species appears to possess a relatively unique optimal set of media requirements, the successful preparation and regeneration of a new species cannot be necessarily inferred from the successful regimens applied to unrelated plant varieties.

Despite the recent advances in plant regeneration for a variety of species, corn (*Zea mays*) is one of the crops which has been refractory to regeneration protocols; hence, the application of plant cell culture for improvement of the majority of pure lines and commercial hybrids of this crop has lagged behind that progress in the field in general.

Absent a functioning regeneration protocol, more traditional avenues for crop improvement have been utilized. One approach has been to introduce into the commercial corn genome agronomically useful characteristics derived from exotic or "wild" Zea germplasm by conventional sexual hybridization and back-crossing breeding procedures. One source of exotic germplasm which has been employed is teosinte (Zea spp.) Teosinte has been described as a possible ancestor of today's modern *Zea mays* forms. There are several known races of teosinte that are either annual and diploid or perennial and tetraploid. A new teosinte that is both diploid and perennial (*Zea diploperennis*) has recently been discovered (Iltis, H. H., et al. *Science* 203: 186–188 (1979)). This species can be sexually hybridized with commercial corn. Interspecies hybrids between *Z. mays* and *Z. diploperennis* are fertile and based on nearly complete chromosome pairing will be potentially useful for crop improvement (Pasupulet, C. V. and W. C. Galinat, *J. of Heredity* 73:168–70 (1982) and Galinat, W. C. and C. V. Pasupulet *Maydica* 27:213–220 (1982)). Among the more useful traits for which *Zea diploperennis* may serve as a source include, resistance to maize chlorotic dwarf, maize chlorotic mottle, and maize streak viruses, and maize bushy stunt mycoplasma as well as tolerance to maize raydo fino virus. Unfortunately, even though *Zea diploperennis* possesses valuable genetic potential for corn improvement, by being limited to conventional breeding techniques, it will require years to develop the improved lines.

It is, therefore, highly desirable to discover conditions which will permit the regeneration of *Zea diploperennis* from tissue culture thereby allowing the full range of biotechnological techniques to be brought to bear on the breeding process; thereby significantly reducing the time required to recover improved breeding lines.

The culture of the diploid and annual teosinte (*Zea mexicana*) was undertaken (Cure, W. W. and R. L. Mott *Physiol Plant.* 42:91–96 (1978)) and limited callus-like growth was reported but no shoot regeneration occurred. It was also reported (Dhaliwal, H. S. and H. Lorz, *Maize Genetics Coop. Newsletter* 53:144 (1979)) that scutella cultures of immature embryos of $F_1$ hybrids between teosinte (*Z. mexicana*) 'El Salado' and the inbred corn line 'B-73' regenerated numerous plantlets. Shoot culture was also tested with mature seeds of B-73, El Salado and B-73 x El Salado. B-73 corn tissues had no response while El Salado and hybrid tissues gave similar results as those described for immature embryo cultures.

It has not heretofor been possible to employ somatic tissue from field grown plants of *Zea diploperennis* as a source of material for plant regeneration from tissue culture.

The term "plant tissue culture" as used herein is taken in its broadest meaning to refer to the cultivation, in vitro, of all plant parts, whether a single cell, a tissue or an organ, under aseptic conditions. More restrictive terms relating to plant tissue culture technology include: "callus culture" by which is meant, the culture of cell masses on agar medium and produced from an explant of a seedling or other plant source; "cell culture" by which is meant, the culture of cells in liquid media in vessels which are usually aerated by agitation; "organ culture" by which is meant, the aseptic culture on nutrient media of anthers (microspores), ovaries, roots, shoots, or other plant organs; "meristem culture and morphogenesis" by which is meant, the aseptic culture of shoot meristems or other explant tissue on nutrient media for the purpose of growing complete plants, and "protoplast culture" by which is meant, the aseptic isolation and culture of plant protoplasts from cultured cells or plant tissue.

BRIEF DESCRIPTION OF THE INVENTION

This invention provides a method for the controlled regeneration of hybrids of *Zea diploperennis* comprising:

forming callus from explant tissue on a first callus promoting medium subculturing said callus inducing plantlet regeneration by transferring said callus to a second regeneration promoting medium inducing shoot and root formation by transferring said plantlets to a third root promoting medium.

DETAILED DESCRIPTION OF THE DRAWINGS

Figure 1:
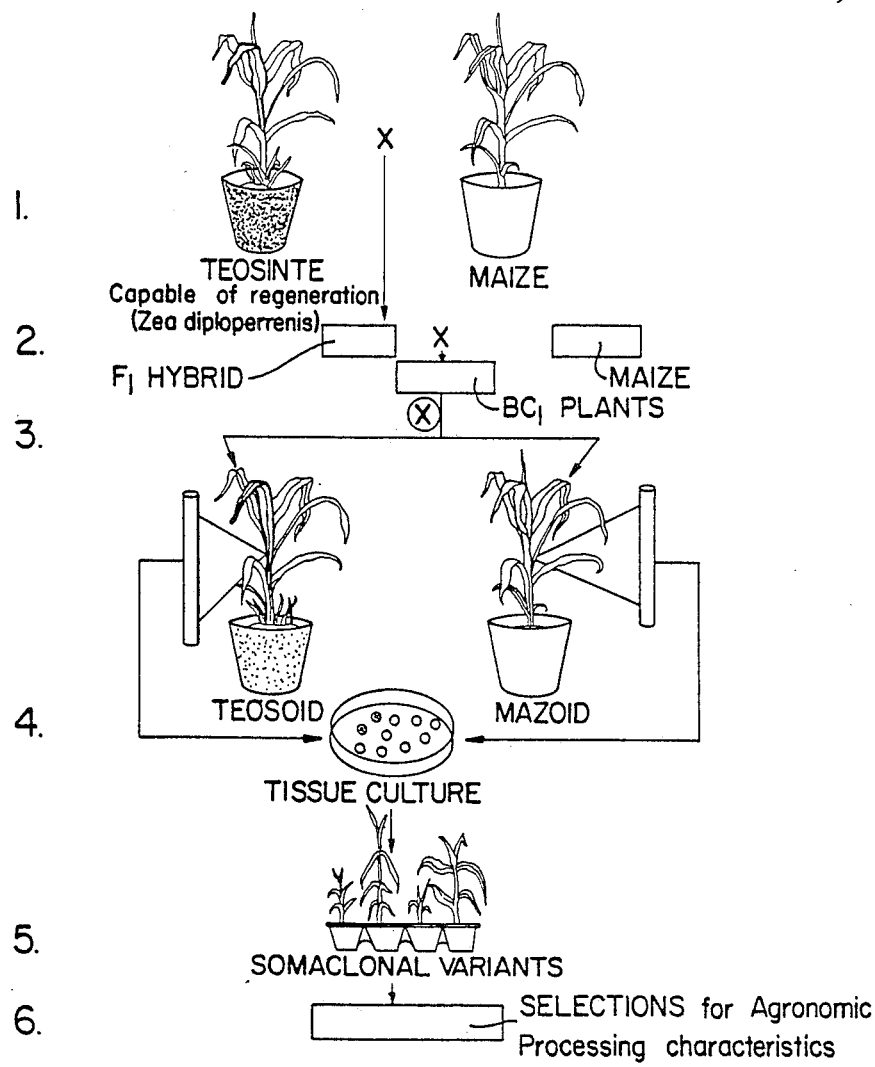

FIG. 1 - This figure illustrates the combination of the tissue culture and breeding strategies for corn improvement.

Figure 2:
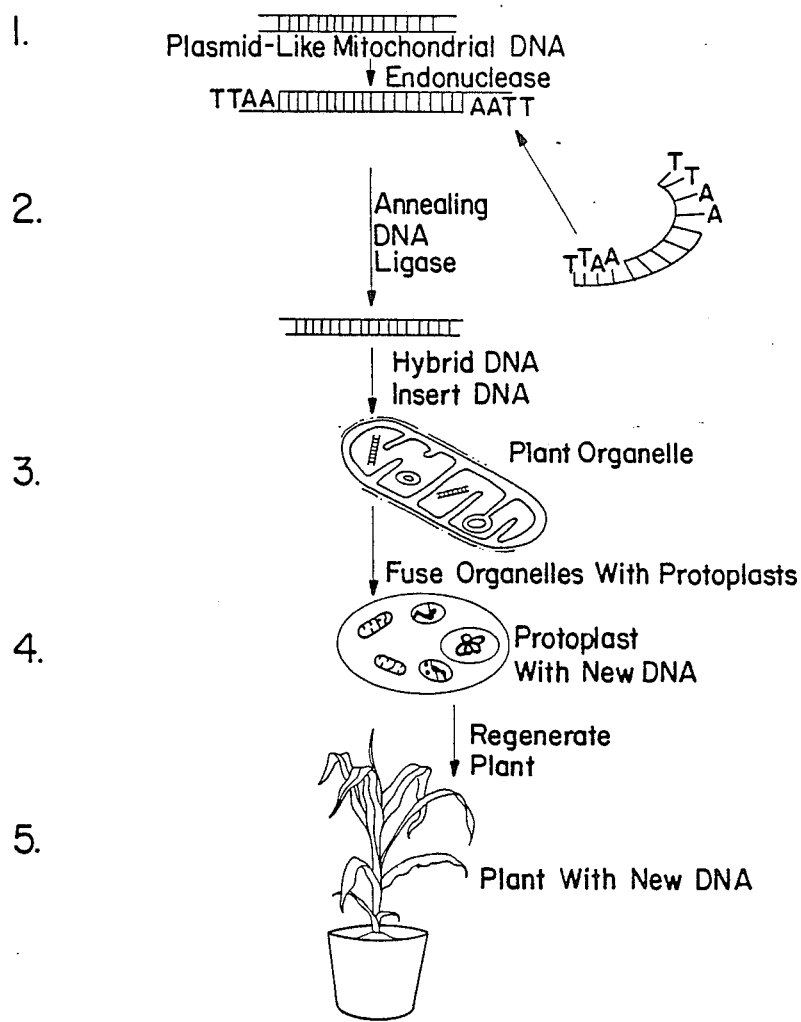

FIG. 2 - This figure illustrates a protocol for gene transfer in corn.

DETAILED DESCRIPTION OF THE INVENTION

On their face, the principles underlying plant tissue culture are quite simple. Initially, it is necessary to isolate a plant part from the intact plant and disrupt its organ, inter-tissue, or inter-cellular relationships. Subsequently, it is necessary to provide the isolated material with the appropriate environment in which to express its intrinsic or induced developmental potential. Finally, the steps must be carried out aseptically. Although the principles may be simply stated, as a matter of practice, the successful culture of plant tissue and its regeneration into a mature plant is extremely complex.

The regeneration may be envisioned to comprise three stages. The first stage occurs following the transfer of an explant onto a culture medium. This stage is characterized by a proliferation of the explant or callus. The second stage is characterized by a rapid increase in organ growth. This stage may require a transfer to a second medium with or without a change in growth regulator concentration. The final stage occurs when the plants are removed from in vitro culture and requires the establishment of the autotrophic state.

A number of experimental parameters must be addressed during the regeneration protocol. For example, for a particular species the source of the explant may be important for the success of the subsequent regeneration. The size and the shape of the explant may also be critical. Another element to be considered is the method of providing aseptic explant material for purpose of callus formation. This involves sterilization of the explant tissue prior to inoculation onto propagation medium. Even this apparently routine process is subject to a wide variety of critical experimental parameters.

It is an object of this invention to provide a method for the regeneration of somatic cells of *Zea diploperennis* hybrids or hybrids derivatives from tissue culture. *Zea diploperennis* hybrid derivitives as used herein refers to the progeny of from 1 to 5 backcrosses and/or selfings of a *Zea diploperennis* x commercial corn variety (*Zea mays*) $F_1$ plant. It is a further object to use *Zea diploperennis* as a genetic bridge to introduce not only disease resistance and other agronomically useful traits such as high tillering capacity into a wide variety of commercial lines of corn but to transfer plant regeneration capacity to said commercial lines as well. Other embodiments of this invention include: The use of $F_1$ or backcross (BC) plants of *Zea mays* x *Z diploperennis* as donor tissue to generate and recover somaclonal variants from regenerated somatic cells; and the use of plasmid-like DNA in the mitochondria of *Zea diploperennis* as a vector for recombinant DNA-based technology.

Apical stem sections of field grown teosinte plants (*Zea diploperennis*) were collected as donor tissue and external leaves and leaf sheaths were removed. Stem segments of 5-8 cm were cut, rinsed for 3 min. with 1% laboratory detergent and washed twice with tap water. These small stem segments were then transferred to a fungicide solution (Captan 0.5 g/1) for 30 min. with agitation. After three rinsings with sterile water, the stem segments were sterilized in a solution of 2.5% sodium hypochlorite for 30 min. and then dissected. The apical and lateral sub-meristems (3-4 leaf primordia; ca. 1-3 mm long) were aseptically excised using a stereoscope. The meristem explants were placed on a basal salts medium (See Table I) containing sucrose (2.5 or 10%), pyridoxine (5 $\mu$M), thiamine HCl (1 $\mu$M), nictotinic acid (1 $\mu$M), inositol (50 $\mu$M), agar (0.7%) and various concentrations of 2,4-D between 2.5 and 20 $\mu$M. The pH was adjusted to 5.8 before autoclaving. A filter sterilized solution of L-asparagine (1 $\mu$M) was added to some replicates of each 2,4-D treatment. Thirty replicates for each treatment were incubated in the dark at 27°±1° C. and transferred to fresh medium every 21-18 days. Plant regeneration was obtained on secondary MS medium devoid of 2,4-D grown under 2:1 fluorescent/incandescent light (8-10 W/m$^2$), 16 h photoperiod.

Although several additional basal salts media are known including but not limited to, B5 medium, White's medium and Schenk-Hilderbrandt medium (See, e.g., Gamborg, O. L. et al., (1976), In Vitro 12: 473-478); the preferred medium is that described by Murashige, T. and Skoog, F., (1962), Physiol. Plant. 15: 473-497 (MS medium).

TABLE 1
COMPOSITION OF MS SALT MEDIUM
(MURASHIGE, T., and, F. SKOOG, PHYSIOL. PLANT. 15: 473-497 (1962))

| MACRO-NUTRIENTS | mM | mg/l |
|---|---|---|
| NH$_4$NO$_3$ | 20.6 | 1650 |
| KNO$_3$ | 18.8 | 1900 |
| CaCl$_2$.2H$_2$O | 3.0 | 440 |
| MgSO$_4$.7H$_2$O | 1.5 | 370 |
| KH$_2$PO$_4$ | 1.25 | 170 |

| MICRO-NUTRIENTS | $\mu$M | mg/l |
|---|---|---|
| KI | 5 | 0.83 |
| NH$_3$BO$_3$ | 100 | 6.3 |
| MnSO$_4$.4H$_2$O | 100 | 23.3 |
| MnSO$_4$.H$_2$O | — | — |
| ZnSO$_4$.7H$_2$O | 30 | 8.6 |
| Na$_2$Mo$_4$.2H$_2$O | 1.0 | 0.25 |
| MoO$_3$ | — | — |
| CuSO$_4$.5H$_2$O | 0.1 | 0.025 |
| CoSO$_4$.6H$_2$O | 0.1 | 0.025 |
| Fe$_2$(SO$_4$)$_3$ | — | — |
| Na$_2$EDTA | 100 | 37.3 |
| FeSO$_4$.7H$_2$O | 100 | 27.8 |

The proliferation of callus tissue from submeristem explants of diploid perennial teosinte was observed in 25-30 day old cultures in media supplemented with 2.5 to 40 $\mu$M 2, 4-D. As this species has multiple tillers, it is possible by removing explants from one stem to obtain somatic tissue regeneration without destroying the donor plant. Immature influorescence is often used as a somatic explant to establish cell cultures of Gramineae. However, stem tissue, available throughout the growth cycle, is a more suitable donor tissue than immature influorescence which is only available during the flowering period.

Suitable callus proliferation and survival was only observed in cultures grown on the 2,4-D containing media at 2.5 to 10 μM concentrations. No significant differences were found in the quality of callus formation from cultures growing in this range of 2,4-D concentrations. Callus formation in primary medium was very limited at 20-40 μM 2, 4-D or failed to proliferate 75-200 μM 2, 4-D. For all treatments, low levels of sucrose (2%) provided better callus initiation and proliferation than high levels of sucrose (20%). L-asparagine had no influence on callus growth.

During first to second subcultures in the primary medium, the tissue has a white-creamish color and a semi-friable consistency. Callus cultures with a watery appearance did not grow further under a regime of periodic subcultures. Semi-friable callus ca. 1-2 cm in diameter was observed after 50-60 days in culture (second subculture). Callus tissues became more friable after 3-4 subcultures on primary medium and some cultures could be identified that contained areas of white tissue that were slightly different from the rest of the callus mass.

Plant regeneration was induced from small callus pieces placed on secondary medium (MS Salts, minus 2,4-D) in the presence of light. On this medium, numerous adventitious buds were observed in 30% of cultivated flasks after a few days. The growth and development of these adventitious buds led to the development of multiple shoots (5-6 plants/culture) with the light-green leaves. Curled and wrinkled white leaves were frequently observed. These white tissues and leaves were very similar to the ones observed for Zea mays cultures initiated from immature embryos in medium containing 2,4-D (Green, C. E. and R. L. Phillips, Crop Sci. 15: 417-21 (1975)). Green leafy structures were observed before he development of shoots. These leaf structures have been described as scutella of precociously germinating embryos in tissue cultures of wheat and pearl millet.

Plantlets with first leaves 1-2 cm long were transferred to a tertiary medium (half-strength MS, with 2% sucrose). A few days later, several shoots were observed including a few that already initiated roots. Isolated shoots were rooted in the same tertiary medium. In a "potting-up" procedure, the regenerated plants were removed from agar jars, washed thoroughly in tap water, and immediately transferred to a Promix soil mixture in 4 gallon pots. Under greenhouse conditions, the tissue-culture-derived plants grew very fast reaching ca. 80 cm height after 50 days. At this time, 11-16 multiple tillers were observed among the regenerated greenhouse plants.

The development of high frequency plant regeneration from cultured somatic tissues of Zea diploperennis as described above offers new possibilities for plant regeneration from protoplast fusion products of wild species and commercial lines of corn as well as $F_1$ and $BC_1$ progeny of Zea diploperennis and commercial lines of corn. These possibilities are predicated on the observation that plant regeneration appears to behave as a dominant trait in interspecies hybrids with teosinte, thus construction of such hybrids would facilitate the selective transfer of genes governing regeneration into commercial cultivated corn varieties. Introduction of $F_1$ hybrids of barley into culture has already been shown to result in chromosome loss in regenerated plants (Orton, T. J., Theoret. Appl. Genet. 56:101-112 (1980)).

The $F_1$ or $BC_1$ plants of corn x Z. diploperennis are also useful as donor tissue to recover novel somaclonal variation. Somaclonal variation has been reported among plants regenerated from immature embryos of corn and both single gene mutations and cytoplasmic DNA changes were observed (Edallo, S. et al. Maydica 26:39-56 (1981) and Umbeck, P. F., and B. G. Gengenbach, Crop Science 23:584-588)). In addition, this invention contemplates the recovery of new types of recombinants in plants regenerated from anthers of $F_1$ hybrids or $BC_1$ plants.

Employing the regeneration protocol described above, conventional bleeding may be coupled with somaclonal variation to establish new breeding lines. The culture of somatic tissues of segregating sexual hybrids and backcrosses of corn and teosinte are particularly useful in this regard. As outlined in this scheme (FIG. 1) the most suitable BC1 or mazoid or teosoid backcrossed plants are identified in the field and selected plants are used as donor tissue for somaclonal variation using mature tissues. Somaclonal variants are selected for processing characters and agronomically important traits such as disease resistance.

The following steps comprise the selection strategy for corn improvement and are illustrated in FIG. 1.

(1) Identify superior corn and Z. diploperennis germplasm. Cross parent lines to produce an $F_1$ hybrid.
(2) Backcross hybrid to maize.
(3) Self-fertilize backcrosses for one to five generations and select for mazoid and teosoid type plants.
(4) Introduce stem segments or immature embryos of donor tissue into cell culture.
(5) Regenerate plants and self fertilize to identify somaclonal variants.
(6) Select desirable somaclones from replicated field plots.

To illustrate this aspect of the invention further, a cross of Zea mays c.v. maya x Zea diploperennis was made employing Z. diploperennis as the male parent. The $F_1$ was backcrossed to the Zea mays parent and the progeny selfed for two further generations. The resultant progeny where classified as mazoid or teosoid type depending on whether the overall phenotype was more like maize or more like teosinte. Some of the resulting teosoid progeny were further crossed to a Zea mays sugary variant and the resulting hybrid was denominated a teosoid hybrid (sugary type).

The Zea mays parental type, the teosoid hybrids resulting from the two selfing of the $F_1$ backcross hereinafter referred to as the teosoid hybrid (normal type) and the teosoid hybrid (sugary type) were each selfed and immature embryos recovered as donor tissue and introduced into tissue culture as described above for Zea diploperennis Table 2 shows the regeneration frequencies for various Zea diploperennis hybrids as compare to the Zea mays control.

Although immature embryos were employed as donor tissue, as demonstrated above somatic nonembryo tissues, such as apical stem sections, are also useful as sources of donor tissue.

| REGENERATION FREQUENCIES OF MAIZE AND TEOSINTE/MAIZE HYBRID TISSUES | | | | | |
|---|---|---|---|---|---|
| Genotype | No. explants | Total no. callus | Regenerating callus | | Total No. green shoots |
| | | | No. | % | |
| MAIZE (dent type) | 40 | 46 | 0 | 0 | 0 |
| TEOSOID HYBRID (normal type) | 187 | 368 | 93 | 25 | 129 |
| TEOSOID HYBRID (sugary type) | 46 | 133 | 65 | 49 | 105 |

In a further embodiment, the regeneration protocol supra is employed with recombinant DNA techniques to achieve genome modification in corn.

*Zea diploperennis* is particularly attractive for such recombinant DNA studies due to the recent report of plasmid-like mitochondrial DNA in this species (Timothy, D. H. et al. *Maydica* 28:139-49 (1983)). A scheme demonstrating the gene transfer utilizing the plasmid-like DNA is depicted in FIG. 2. Plasmid-like DNAs are isolated from mitochondria, genetically modified, and then reintroduced into corn organelles.

The following steps comprise the transfer strategy and are illustrated in FIG. 2.

(1) Plasmid-like DNA occurring in *Z. diploperennis* mitochondria is isolated.
(2) Donor DNA is combined with plasmid-like DNA to produce new hybrid DNA.
(3) The hybrid DNA is reintroduced into isolated corn mitochondria.
(4) The isolated, modified mitochondria are reintroduced into corn of *Z. diploperennis* protoplasts.
(5) The modified protoplasts are regenerated into new plants containing modified DNA.

The plasmid-like DNA may be isolated according to the procedure fo Timothy et al. supra, and the hybrid DNA molecules are produced by methods well-known to workers in the art. See for example *Molecular Cloning: A Laboratory Manual*, T. Maniatis et al., Cold Spring Harbor Laboratory, 1982, the contents of which we incorporated herein by reference. Briefly the procedure comprises subjecting both the donor DNA and the plasmid-like DNA to the action of restriction endonucleases, mixing the DNAs to permit the association of the donor DNA with the plasmid-like DNA and ligating the recombinant molecules by treatment with DNA ligase.

Once the hybrid DNA is reintroduced into mitochondria and the modified mitochondria are subsequently reintroduced to *Z. diploperennis* protoplasts; the modified protoplasts are regenerated according to the method described herein.

What is claimed is:

1. A method for the controlled regeneration of *Zea diploperennis interspecific* hybrids or hybrid derivitives comprising:
   forming callus from explant tissue obtained from said hybrids or hybrid derivatives on a first callus promoting medium supplemented with 2,4-D;
   subculturing said callus;
   inducing plantlet regeneration by transferring said callus to a second regeneration promoting medium characterized by the absence of 2,4 -D; and
   inducing shoot and root formation by transferring said plantlets to a third root promoting medium.

2. The method of claim 1 which includes the further step of recovering the regenerated plantlet from the rooting medium and potting-up same to provide corn plants.

3. The method according to claim 1 wherein said first callus promoting medium comprises a Murashige-Skoog salts medium supplanted with sucrose, pyridoxine, thiamine, nicotinic acid, inositol, 2,4-dichlorophenoxy acetic acid (2,4-D), and agar.

4. The method according to claim 3 wherein the 2,4-D is present in a concentration for about 1 to about 40 $\mu$M.

5. The method according to claim 4 wherein the 2,4-D is present in a concentration from about 1 to about 10 $\mu$M.

6. The method according to claim 3 wherein the sucrose is present in an amount from about 2% to about 10%.

7. The method according to claim 6 wherein the sucrose is present in an amount of about 2%.

8. The method of claim 1 wherein the callus forming step is conducted in the dark.

9. The method of claim 1 wherein the subculturing step comprises 1 to 5 subculturing periods on callus promoting medium.

10. The method of claim 9 where a single subculturing period comprising culturing the callus on said callus promoting medium for a period of from about 25 to about 30 days.

11. The method of claim 1 wherein the regeneration promoting medium comprises a Murashige-Skoog salts medium supplement with sucrose, pyridoxine thiamine, nicotinic acid, inositol and agar.

12. The method of claim 11 wherein the sucrose is present in an amount from about 2% to about 10%.

13. The method of claim 12 wherein the sucrose is present in an amount of about 2%.

14. The method of claim 1 wherein the plantlet regeneration step is conducted partially in the light.

15. The method of claim 14 wherein the regeneration step is characterized by a 16 hour photoperiod of 2:1 fluorescent/incandescent light.

16. The method of claim 1 wherein said root promoting medium comprises one-half strength MS salts medium supplemented with about 2% sucrose.

* * * * *